US010506966B2

(12) United States Patent
Gore et al.

(10) Patent No.: US 10,506,966 B2
(45) Date of Patent: Dec. 17, 2019

(54) METHODS AND SYSTEMS FOR DETERMINING SENSORY MOTOR PERFORMANCE BASED ON NON-POSTURAL INFORMATION

(71) Applicants: Emory University, Atlanta, GA (US); Georgia Tech Research Corporation, Atlanta, GA (US)

(72) Inventors: Russell K. Gore, Atlanta, GA (US); Michelle LaPlaca, Atlanta, GA (US); David W. Wright, Atlanta, GA (US); Tamara Espinoza, Atlanta, GA (US); Shean Phelps, Atlanta, GA (US); Brian Liu, Atlanta, GA (US); Stephen Smith, Atlanta, GA (US); Nicole Kosoris, Atlanta, GA (US); Alessio Medda, Atlanta, GA (US); Courtney Crooks, Atlanta, GA (US)

(73) Assignees: Emory University, Atlanta, GA (US); Georgia Tech Research Corporation, Atlanta, GA (US)

( * ) Notice: Subject to any disclaimer, the term of this patent is extended or adjusted under 35 U.S.C. 154(b) by 83 days.

(21) Appl. No.: 15/510,396

(22) PCT Filed: Sep. 11, 2015

(86) PCT No.: PCT/US2015/049704
§ 371 (c)(1),
(2) Date: Mar. 10, 2017

(87) PCT Pub. No.: WO2016/040815
PCT Pub. Date: Mar. 17, 2016

(65) Prior Publication Data
US 2017/0281069 A1 Oct. 5, 2017

Related U.S. Application Data

(60) Provisional application No. 62/049,541, filed on Sep. 12, 2014.

(51) Int. Cl.
*A61B 5/11* (2006.01)
*A61B 5/00* (2006.01)

(52) U.S. Cl.
CPC .......... *A61B 5/4023* (2013.01); *A61B 5/1116* (2013.01); *A61B 5/1124* (2013.01);
(Continued)

(58) Field of Classification Search
CPC .......... A61B 5/1116; A61B 2562/0219; A61B 5/1124; A61B 5/4023; A61B 5/1114;
(Continued)

(56) References Cited

U.S. PATENT DOCUMENTS 6,067,986 A * 5/2000 Kluger ................ A61B 5/1124
600/595
7,720,530 B2 5/2010 Causevic
(Continued)

OTHER PUBLICATIONS

International Search Report & Written Opinion for PCT Application No. PCT/US2015/049704 dated Sep. 11, 2015.

*Primary Examiner* — David J. McCrosky
(74) *Attorney, Agent, or Firm* — Emory Patent Group

(57) ABSTRACT

Methods and systems relate to determining sensory motor performance based on user non-postural movements within a generated dynamic virtual environment. The generated environment requires users to: (i) utilize primary sensor inputs (e.g., vision, vestibular sensation and somatosensation); (ii) assess the dynamic virtual environment; and (iii) integrate and translate those inputs into movement to control the dynamic virtual environment. The methods may include receiving non-postural user input with respect to a state of one or more attributes of a dynamic virtual environment provided on a user interface for one or more sessions, the one or more attributes including a control object and a target which moves with respect to the control object; determining performance information based on the user input and the
(Continued)

state of the one or more attributes for the one or more sessions; and determining sensory motor performance information from the performance information.

20 Claims, 14 Drawing Sheets

(52) U.S. Cl.
CPC .......... *A61B 5/7475* (2013.01); *A61B 5/1113* (2013.01); *A61B 5/1114* (2013.01)

(58) Field of Classification Search
CPC ... A61B 5/1118; A61B 5/1122; A61B 5/1126; A61B 5/743; A61B 5/7475; A61B 5/112; A61B 5/1121; A61B 5/1127; A61B 5/1128; A61B 5/1036; A61B 5/4076; A61B 5/4082; A61B 5/4088; A61B 5/486; A61B 5/744; A61B 5/748; A61M 2230/62

See application file for complete search history.

(56) References Cited

U.S. PATENT DOCUMENTS

| | | |
|---|---|---|
| 8,568,311 B2 | 10/2013 | LaPlaca et al. |
| 2006/0022833 A1* | 2/2006 | Ferguson .............. A61B 5/1124 340/573.1 |
| 2010/0121415 A1 | 5/2010 | Skelton et al. |
| 2012/0089049 A1 | 4/2012 | Suarez et al. |
| 2012/0238831 A1 | 9/2012 | Benford |
| 2013/0023740 A1 | 1/2013 | Kirchner et al. |
| 2015/0040685 A1 | 2/2015 | Nicholson et al. |

* cited by examiner

METHODS AND SYSTEMS FOR DETERMINING SENSORY MOTOR PERFORMANCE BASED ON NON-POSTURAL INFORMATION

CROSS-REFERENCE TO RELATED APPLICATIONS

This application is the National Stage of International Application No. PCT/US2015/049704 filed Sep. 11, 2015, which claims priority to U.S. Provisional Application No. 62/049,541 filed Sep. 12, 2014. The entirety of each of these applications is hereby incorporated by reference for all purposes.

ACKNOWLEDGEMENTS

This invention was made with government support under Grant No. W81XWH-12-C-0203 awarded by the United States Army. The government has certain rights in the invention.

BACKGROUND

Vestibular function, measured through balance and the vestibulo-ocular (VO) system, can be considered an important part of concussion testing. Balance and vestibular complaints are generally common after concussion/mild traumatic brain injury (mTBI) of patients in the immediate post injury period. Many patients can have symptoms of persistent dizziness, imbalance, and postural instability. Many assessments of balance require users to stand or perform a series of standing postures. These tests can be problematic for patients that are dealing with these dizziness symptoms, with orthopedic injuries (e.g., ankle injuries), or with hostile environments (e.g., military personnel in war zones).

SUMMARY

Thus, there is need for a system that can determine sensory motor performance, for example, balance, without requiring the patient to stand or perform a series of standing postures.

The disclosure relates to systems and methods that can provide a sensory motor assessment based on non-postural data. The systems and methods can determine sensory motor performance based on non-postural movements within a dynamic virtual environment provided on a user interface.

In some embodiments, the method may include receiving performance information with respect to a dynamic virtual environment. The performance information may include user input data with respect to a state of one or more attributes of a dynamic virtual environment provided on a user interface for one or more sessions and the state of the one or more attributes. The one or more attributes may include a control object that is moved directly based on user input and a target which moves with respect to and based on a movement of the control object, the user input relating to non-postural movement. The method may also include determining one or more performance variables based on the performance information and determining sensory motor performance information from the one or more performance variables. The method may be performed by a computer having a processor and a memory. The user inputs may be received by a user device having an IMU device.

In some embodiments, the system may include at least one processor and a memory. The processor may be configured to cause receiving performance information with respect to a dynamic virtual environment. The performance information may include user input data with respect to a state of one or more attributes of a dynamic virtual environment provided on a user interface for one or more sessions and the state of the one or more attributes. The one or more attributes may include a control object that is moved directly based on user input and a target which moves with respect to and based on a movement of the control object, the user input relating to non-postural movement. The processor may further be configured to cause determining one or more performance variables based on the performance information and determining sensory motor performance information from the one or more performance variables. The user inputs may be received by a user device having an IMU device.

In some embodiments, the disclosure may relate to a computer-readable medium storing instructions for receiving performance information with respect to a dynamic virtual environment. The performance information may include user input data with respect to a state of one or more attributes of a dynamic virtual environment provided on a user interface for one or more sessions and the state of the one or more attributes. The one or more attributes may include a control object that is moved directly based on user input and a target which moves with respect to and based on a movement of the control object, the user input relating to non-postural movement. The instructions may further include determining one or more performance variables based on the performance information and determining sensory motor performance information from the one or more performance variables. The user inputs may be received by a user device having an IMU device.

Additional advantages of the disclosure will be set forth in part in the description which follows, and in part will be obvious from the description, or may be learned by practice of the disclosure. The advantages of the disclosure will be realized and attained by means of the elements and combinations particularly pointed out in the appended claims. It is to be understood that both the foregoing general description and the following detailed description are exemplary and explanatory only and are not restrictive of the disclosure, as claimed.

BRIEF DESCRIPTION OF THE DRAWINGS

The disclosure can be better understood with the reference to the following drawings and description. The components in the figures are not necessarily to scale, emphasis being placed upon illustrating the principles of the disclosure.

DESCRIPTION OF THE EMBODIMENTS

Figure 1:
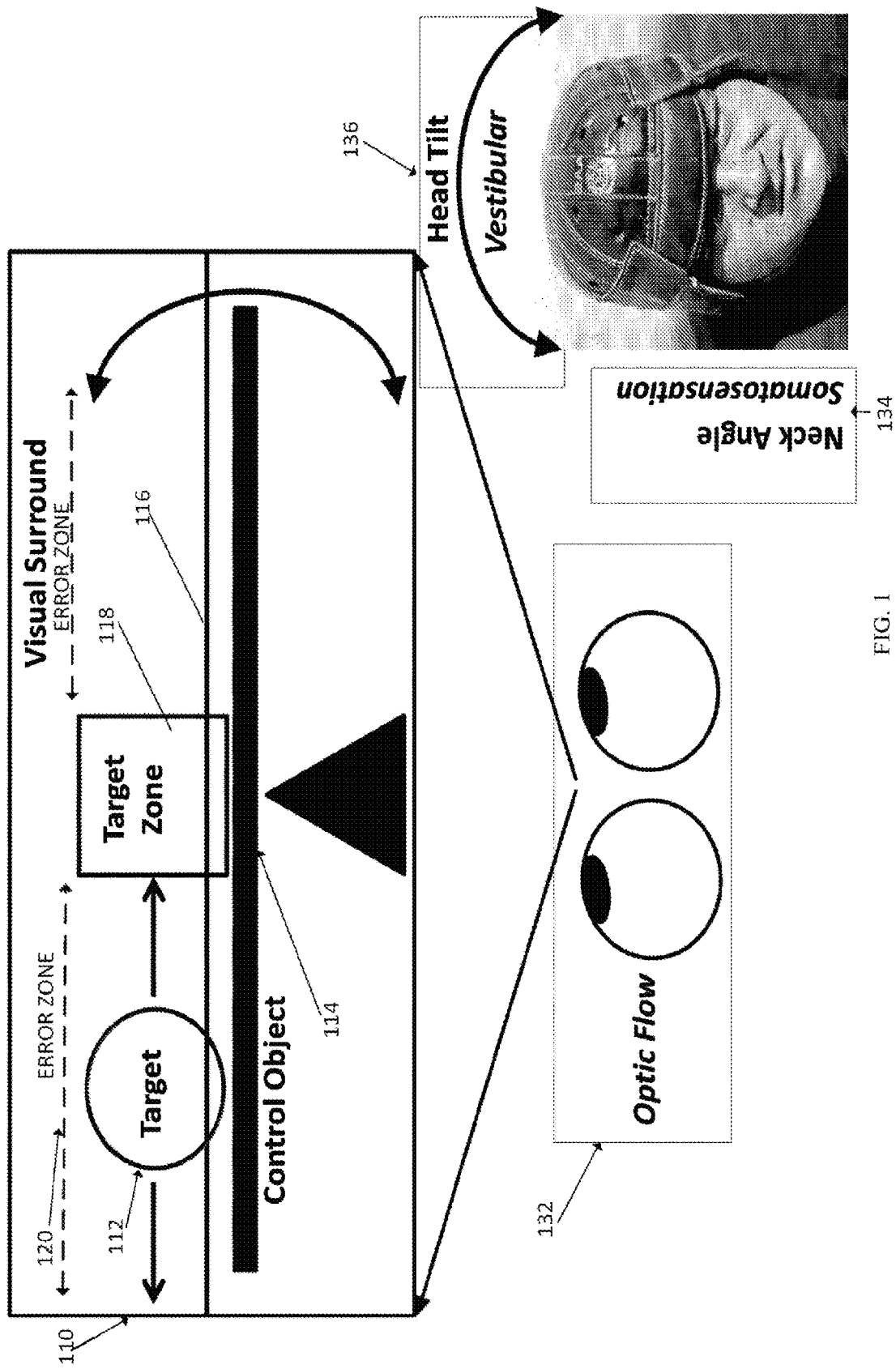
FIG. 1 shows an example of a generated dynamic virtual environment according to embodiments.

In the following description, numerous specific details are set forth such as examples of specific components, devices, methods, etc., in order to provide a thorough understanding of embodiments of the disclosure. It will be apparent, however, to one skilled in the art that these specific details need not be employed to practice embodiments of the disclosure. In other instances, well-known materials or methods have not been described in detail in order to avoid unnecessarily obscuring embodiments of the disclosure. While the disclosure is susceptible to various modifications and alternative forms, specific embodiments thereof are shown by way of example in the drawings and will herein be described in detail. It should be understood, however, that there is no intent to limit the disclosure to the particular forms disclosed, but on the contrary, the disclosure is to cover all modifications, equivalents, and alternatives falling within the spirit and scope of the disclosure.

The disclosure relates to methods, systems, and computer-readable media relate to systems and methods that can determine sensory motor performance, such as human balance, without requiring the user to stand or perform a series of standing postures. The systems and methods according to the disclosure can determine from sensory motor performance, such as human balance, from non-postural movements. Non-postural movements refer to movements not dependent on standing positions or movements; for example, head, neck, or upper extremity movements can be considered non-postural movements. Thus, the systems and methods according to disclosure can avoid testing variability due to other injuries (e.g., orthopedic injuries) that can influence existing balance assessments, such as balance systems based on postural movements. For example, for many systems based on postural movements, a user must stand on an object and prevent sway and movement. A "user" can refer to a patient and/or an individual user for which the sensory motor performance assessment is being performed.

Additionally, the systems and methods can be used in austere and potentially hostile environments encountered in the military in which environmental constraints may prevent an exposed standing balance assessment. The systems and methods can also provide a rapid, mobile, quantitative and/or qualitative measure of sensory motor performance without cumbersome equipment such as standing force plates or problems with reliability encountered with subjective balance assessments. Further applications may include sensory motor assessment during interactions with a dynamic virtual environment such as during train simulations or recreational gaming. In these environments, the systems and methods can provide user specific performance feedback in both real-time and after completion of a specific performance period. The systems and methods can also provide real-time feedback to modify simulation or game play parameters during the performance or game period to facilitate a personalized simulation or gaming experience.

The systems and methods can provide a dynamic visual environment that allows the user to move the head and neck in the physical environment to control. The dynamic visual environment can allow the users to utilize primary sensor inputs (vision, proprioception, and somatosensation) to assess the dynamic virtual environment, and integrate and translate those inputs into movement to control the dynamic virtual environment. The sensory inputs can include but are not limited to vision (e.g., optical flow), vestibular (e.g., input from head movement), and proprioception (e.g., somatosensory input from neck angle). In this way, both the visual environment and the physical environment can be in constant motion, and the interaction between these moving systems can be leveraged to determine sensory motor performance. Sensory motor performance may relate to quantitative or qualitative measurement of a user coordination of a cognitive process and a motor activity that is based on non-postural movement data. For example, sensory motor performance may include but is not limited to a quantitative or qualitative measurement of balance. Additionally, the systems and methods can capture movement information that mirror physiologic inputs during human balance.

In some embodiments, the systems and methods may provide a dynamic virtual environment on a user interface. For example, a dynamic virtual environment may be displayed on a user interface as a two-dimensional or three-dimensional visual display. In some embodiments, the dynamic virtual environment may be displayed on a user interface in an immersive environment. For example, a dynamic virtual environment may be a game or video game interface.

In some embodiments, the dynamic virtual environment may include one or more attributes. The one or more attributes may include a control object, a target (also referred to as "dynamic target"), a target zone (also referred to as "balance zone"), error zone (also referred to as "overshoot"), visual surround, or a combination thereof. The control object (also referred to as "control surface") may be any object or portion of an object that may move directly based on user input. The control object may move with respect to the target and/or the visual surround within the dynamic environment. In some embodiments, the state of the control object (also referred to as "the control object state") may correspond to a position of the control object relative to other attributes of the dynamic virtual environment. The target is an object and/or character within the dynamic virtual environment that may be moved indirectly based on the user input and/or directly by the system or based on movement of the control object. The target may be any object (e.g., ball, wheel, car, path, etc.) and/or character displayed in the virtual environment. The target zone may be a region in the dynamic environment to which the target and/or control object should be moved. The target zone can therefore act as a "goal region," in which if the target is moved, the user is meeting the objective of the game play. In some embodiments, meeting the objective can be considered to be upright and steady (e.g., keeping their balance). In some embodiments, the size and/or location of the target region may be adjustable, for example, may be dependable on the difficulty level associated with the session and/or performance determined by the system (see, e.g., FIG. 6). In some embodiments, the target zone may be a region on the control object (e.g. the balance beam target zone) or a region of interest within the visual environment into which the user is expected to position the dynamic target. The visual surround may relate to the background in the visual environment. The dynamic virtual environment may also include an error zone 120 that refers to one or more areas adjacent to the target zone in which the system considers a user response error (e.g., overshoot) if the user movement data causes the target to move past the target zone into the error zone.

In some embodiments, the system may set one or more conditions associated with a user response error (e.g., overshoot). The conditions may include but are not limited to distance in the error zone and/or outside the target zone with respect to the target zone, time in the error zone and/or outside the target zone, among others, or a combination thereof. For example, the system may determine a user response error if the system determines that the target is in the error zone for a time that meets or exceeds the set period of time and may not determine a user response error if the target is in the error zone for less than that time.

FIG. 1 shows an example of an user interface displaying a dynamic virtual environment 110 according to embodiments. In this example, the dynamic virtual environment relates to balancing a ball on a balance beam. In the environment 100, the target 112 is a ball; the control object 114 is a balance beam; the target zone 118 is a region on the control object (e.g., the balance beam) to which the target should be moved; and the visual surround 116 is the background (e.g., horizon) behind the control object 114 and the target 112. It will be understood that the dynamic target 112, control object 114, target zone, and/or visual surround are not limited to this example (e.g., balancing a ball on a balance beam) and may include other dynamic targets, control objects, and/or target zones.

For example, the dynamic environment may in another form of a simulation or game. By way of example, the dynamic virtual environment may be an aviation game for which the object of the game is to fly the aircraft along a desired flight path. In this example, the desired flight path may be considered the target zone, the wings of the plan may be considered to be the control object, the actual flight path or nose of the aircraft which changes depending on the roll and pitch angle of the wings may be considered to be the dynamic target. The user is instructed to follow the flight path displayed in the visual environment using aircraft control inputs. In this example, the wings, like the balance beam, may be controlled by user input.

In the example, the user using head movement (e.g., head tilts) can cause movement of the beam to cause movement of the ball with respect to the beam. It will be understood that the user can also use different movements to cause changes to the dynamic environment, such as hand movements. In operation, in this example, to cause the ball to move along the balance beam to the target zone, the user can either move their head and/or move the handheld unit to cause the balance beam to move and thereby cause the ball to move along the balance beam. The user movements (inputs) are detected, for example, by a user input device, such an inertial measurement unit (IMU) included in the display device and/or a separate input device, for example, provided in a head-mounted unit or a handheld unit (e.g., computer tablet and/or handheld computer input device).

In some embodiments, the systems according to embodiments generate a dynamic virtual environment that require users: (i) to utilize primary sensor inputs, such as vision (optic flow), proprioception (vestibular sensation), and somatosensation; (ii) to assess the dynamic virtual environment; and (iii) to integrate and translate those inputs into movement to control the dynamic virtual environment. As shown in FIG. 1, the target position 112, the control object state 114, and/or the visual surround 116 provided in the dynamic virtual environment can require users to utilize vision (or optical flow) sensory input 132 to interpret and translate into non-postural movements, such as head and/or hand movement, to cause a change in the target position by causing a change in position of control object 114 (e.g., control object state). In some embodiments, the movements may include head tilt 136 and/or neck angle 134 measured by an inertial measurement unit (IMU) included in the display device and/or a separate input device. In some embodiments, the movements may also include the tilting of a hand held device using hand, wrist, or arm movements measured by an IMU. In some embodiments, the IMU may include but is not limited to an accelerometer, gyroscope, magnetometer, among others, or a combination thereof.

For example, by relying on tilt movements 136 (e.g., head tilt movements), e.g., to change the target position 112 by changing the state of the control object 114 in the dynamic environment 110, the system can require users to utilize vestibular (proprioception) sensory input to interpret and translate into movement. For example, relying on neck angle 134, e.g., to change the target position by changing the control object state, the system can require users to utilize somatosensation sensory input to interpret and translate into movement.

In some embodiments, the systems and methods can determine performance information from the detected user inputs (e.g., head and/or hand movements) 140 with respect to the state of the attributes of the dynamic virtual environment 110. The performance information may relate to the system state and/or user response (e.g., detected user inputs) with respect to a period of time (e.g., one or more increments of time in a session). A session may refer to a time period during which a dynamic environment is presented and generated based on fixed and/or dynamic parameters and data is collected. A time-period for the session may be pre-defined by the system and/or may be defined by the user in real-time (e.g., user decides to end game).

In some embodiments, the performance information may include but is not limited to target position, control object state, user position (e.g., head angular acceleration), or a combination thereof. The target position and control object state may be both relate to the system state and user position may relate to the user state. The target position may relate to the position of the target with respect to the control object and/or target zone. The control object state may correspond to the position of the control object relative to other attributes of the dynamic virtual environment. The user position may relate to detected user inputs (e.g., detected user movement data) in response to the dynamic environment. The user position may include tilt information that can be detected directly via a sensor provided in the user device (e.g., head mounted IMU sensitive to user head tilt or indirectly via a handheld unit including an accelerometer sensitive to tilting of the handheld unit), such as tilt angular acceleration, among others, or a combination thereof.

For example, in response to a system state (e.g., the target position and the control object state), the user can generate a response to change the control object state so that the target (position) moves toward the target zone. For example, in this response, if using a head-mounted IMU, a user moves his head (e.g., tilt) by activating muscles in the neck, resulting in tilt angular acceleration (e.g., head angular acceleration), which can be captured through a sensor, such as an accelerometer. From the detected head movement, neck angle or muscle angle can be indirectly determined from the detected head movement. In another example, in this response, if using a handheld unit, the tilt angular acceleration can correspond to changes in hand, wrist, and/or arm movement that moves the handheld unit and captured by a sensor in the unit (e.g., accelerometer). By way of example, tilt angular acceleration versus target position over time (integrated) can be a surrogate measure of balance using non-postural input data and therefore a sensory motor performance assessment, including balance, can be determined from the performance information without requiring the user to stand.

In some embodiments, the systems and methods can cause the one or more attributes and/or parameters of the dynamic virtual environment to change in response to and/or independently of the user response. For example, one or more attributes may change in a fixed and/or dynamic manner directly in response to and/or independently of user response (e.g., user movement). In this way, the affected sensory inputs may also be controlled.

In some embodiments, the fixed and/or dynamic state of one or more attributes and/or parameters for the dynamic virtual environment for a session may be based on one or more stored testing conditions. The systems and methods can provide one or more testing conditions during different sessions to illicit different user response (e.g., user movement) at one or more different difficulty levels from which the systems and movements can determine performance information. For example, the different levels of difficulty may include easy, medium, hard, and optic flow. For example, the different levels may include a change of one or more parameters: changes to the tilt sensitivity; the dynamic target response to control object changes (e.g. the rolling ball gravity constant); size and/or location of the target zone; the time for completion of the task (e.g., 3 seconds for the ball to reach target zone); other visual environment changes; among others; or a combination thereof. For example, other parameters in the visual environment may include changes to optic flow. The gravity constant may relate to target response to gravity. Changes in the parameters may alter the difficulty of reaching the target zone or alter other attributes of the environment to distract the user from the primary task of reaching the target zone. For example, the time for the target to be in the target zone can change when the system determines an overshoot and user error responses are determined. By way of example, if the time for completion of the task is 3 second, the system may determine an overshoot if the user does not cause the target (e.g., the ball) to reach the target zone within that time period. It will be understood that the time period may be any time period. Also, the system may include a pre-set time period with respect to determination of an overshoot.

In some embodiments, the systems and methods according to embodiments may include changing the tilt sensitivity and/or target response (response to movement of the target). In some embodiments, the systems and methods and methods according to embodiments to calibrate the IMU with respect to the dynamic virtual environment based on the user movement. The systems and methods according to embodiments may adjust the dynamic virtual environment and/or the performance information based on the calibrations. For example, during the calibrations, the IMU can be calibrated at a start of a session to set a "zero" point in terms of tilt. The calibrations may also include determining tilt sensitivity. In some embodiments, the systems and methods may generate a session to be used as a baseline test to determine the tilt sensitivity. Based on the determined tilt sensitivity, the system can modify the control object response to a user input (e.g., head tilt or hand tilt). For example, the system can either quicken and/or slow down the control object response, the target response, and/or a combination thereof. The performance information determined for this baseline session may be processed to determine the optimal tilt sensitivity for a user to maximize difficulty while maintaining average performance (i.e., the game is neither too easy nor too hard). For example, increasing the tilt sensitivity can cause an increase in the control object response to user movement (e.g., a head tilt). In this way, the optimal tilt sensitivity can be user specific. In some embodiments, tilt sensitivity his can also and/or alternatively be used, for example, as a baseline for future assessments. In this way, the individual characteristics of a user can be taken into account when analyzing the performance information to determine sensory motor performance.

During each session, the system generates a dynamic environment for a user interface based on the testing condition. In response to the system state (e.g., target position and control object state) of the dynamic environment, a user may cause the system state to change by user inputs (e.g., user head movements and/user hand movements). The system may detect the user inputs (e.g., movement data) and process the user inputs and/or system state (the target position and control object) state to determine performance information. The system additionally may process the user inputs to cause the system state to change based on the user inputs (e.g., directly change the position of the balance beam and/or indirectly change the position of the ball) (according to the testing condition). The system may continue to update the dynamic environment (e.g., system state) based on the user inputs and detect user movement data to determine performance information until the session period ends. In some embodiments, the system may determine performance information with respect to one or more increments of time during the session period.

In some embodiments, the systems and methods may determine performance assessment information from the performance information. During each session, the systems and methods may determine and store performance information. The performance information may include the user input data, the target position, control object state, environment parameters, among others, or a combination thereof with respect to time. In some embodiments, the performance information may relate to user input data (e.g., non-postural data (e.g., tilt data)) with respect to the system data (e.g., target position and/or control object state and/or environment parameters).

In some embodiments, the systems and methods may determine performance assessment information from the performance information. The performance assessment information may include one or more variables representing user performance during a session. The one or more performance variables may relate to user movement data and target control data with respect to the dynamic environment parameters, among others, or a combination thereof. For example, the one or more performance variables may include determining the user movement and/or target control data with respect to different difficulty condition. For example, the variable(s) may be compared across difficulty levels and after changes in the sensory conditions, such as optic flow changes/variation.

Figure 2A:
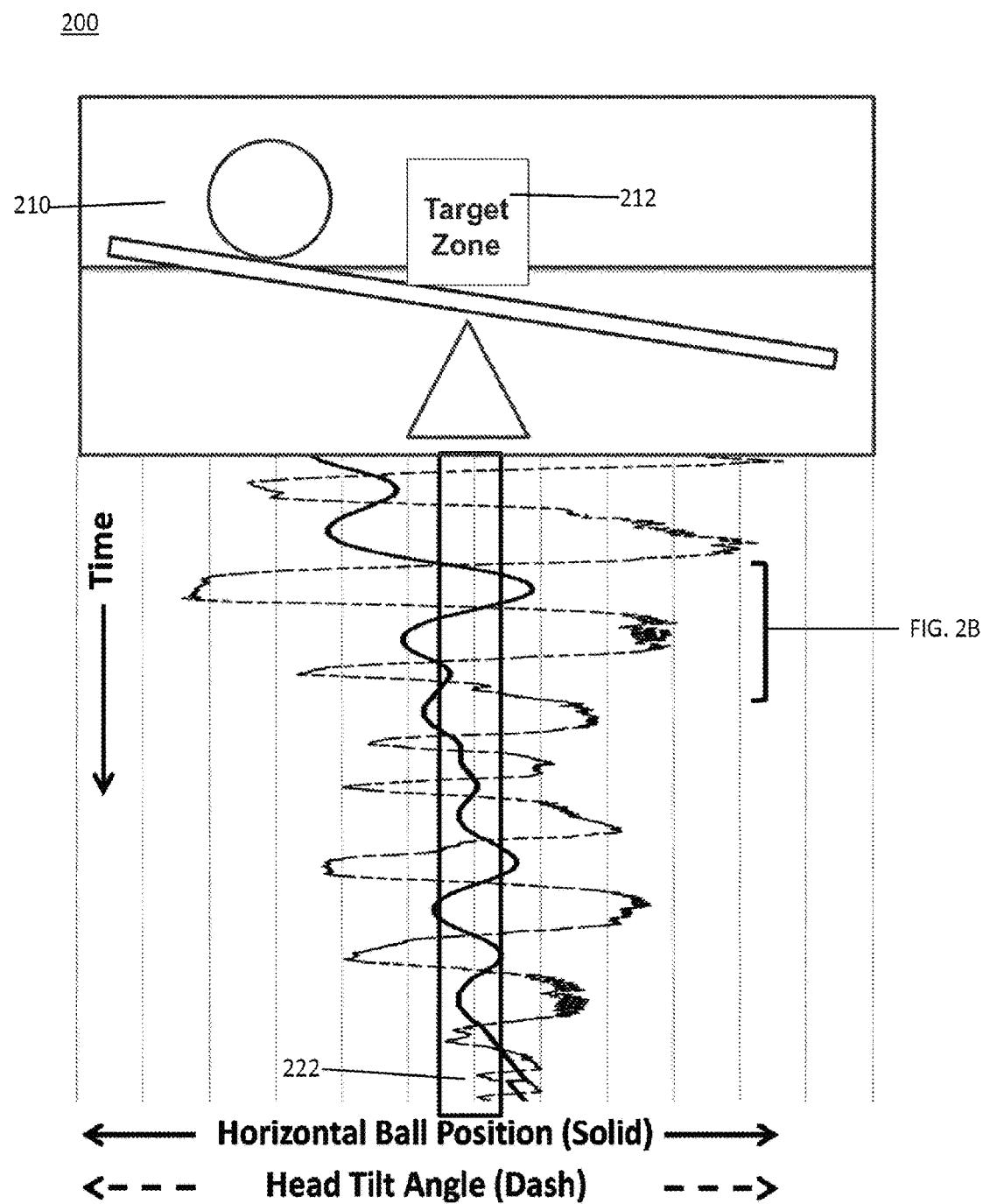
FIGS. 2A and B shows an example of generated dynamic virtual environment with processed user and system state data according to embodiments.
Figure 2B:
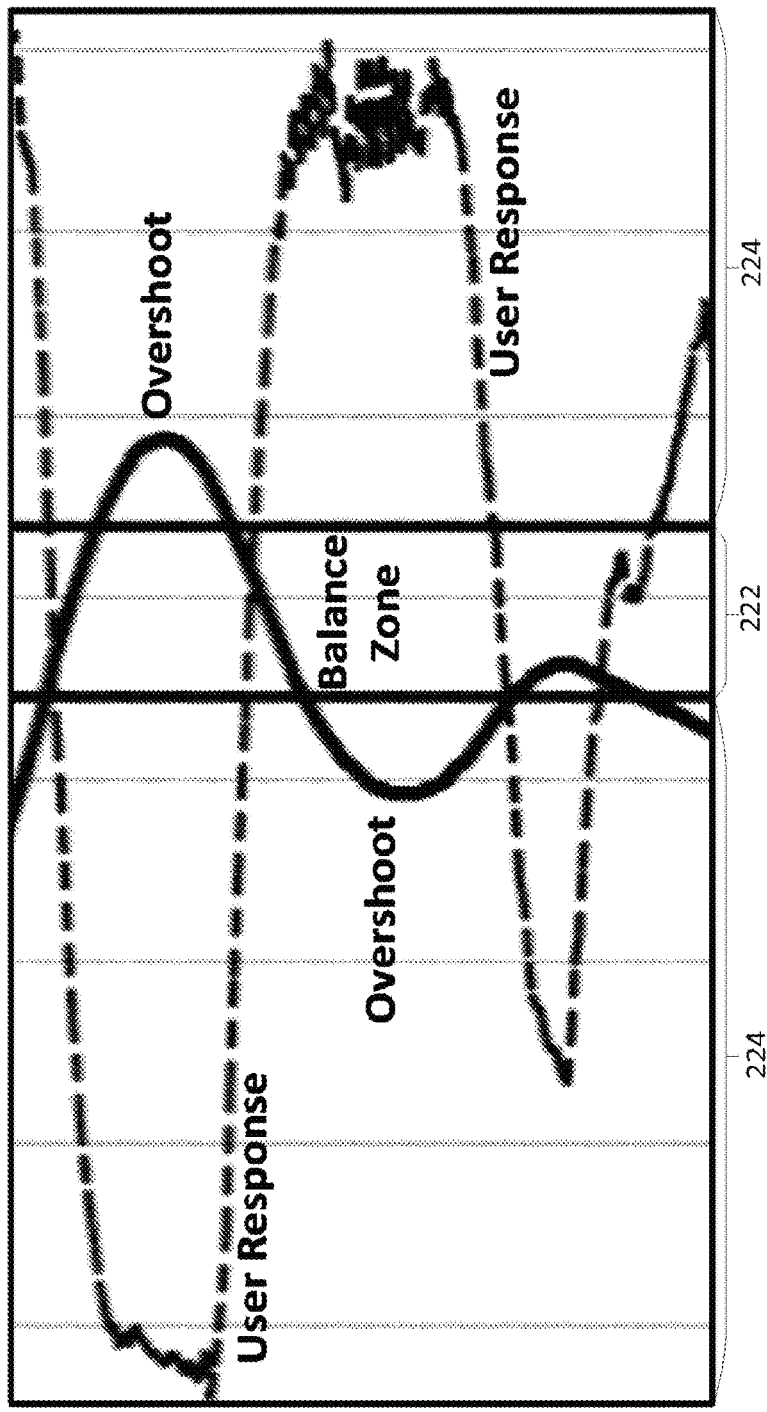

FIGS. 2A and 2B show example 200 of performance information 220 determined during a session in dynamic environment 210, which is similar the dynamic virtual environment shown in FIG. 1; and show example 250, which is an excerpt of the performance information 210 shown in FIG. 2A. As shown in FIGS. 2A and 2B, the region 222 corresponds to the target zone 210 and the regions 224 to the right and left of the target zone 210 represent error responses or overshoots. The solid line represents the target control movement data and the dash line represents the received user input data (determined by an IMU Device) with respect to time.

Figure 3:
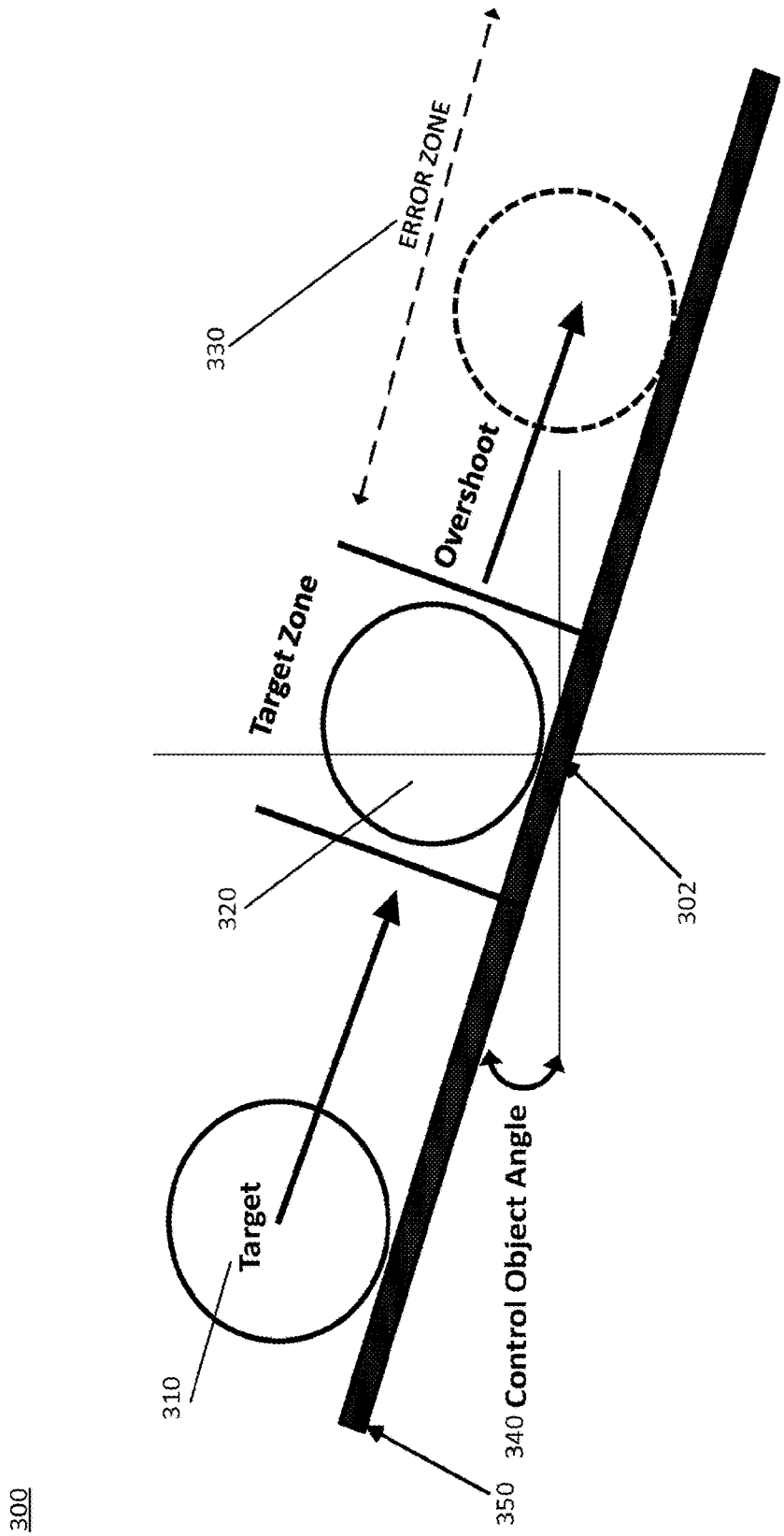
FIG. 3 shows an example of the user performance with respect to a generated dynamic virtual environment according to embodiments.

FIG. 3 shows an example 300 of user input with respect to a dynamic virtual environment generated by the systems and methods and shown in FIGS. 2A and B. For example, as shown in FIG. 3, the system and methods consider an error response (also referred to as "target error response") or overshoot when the target (ball) 310 goes past the target zone 320 into an error zone 330. In the example, the intersection of lines 302 represents the zero point in term of head tilt. Also, as shown in the FIG. 3, the user input (the tilt angle) changes the control object angle 340 of the beam (control object) 350 and thereby changes the position of the beam 350 with respect to the environment. The change in position of the beam 350 can thereby cause a change in position of the target 320 so that moves with respect to the beam 350 and the target zone 320. As shown in FIG. 2B, the system can determine an overshoot based on the target control data (e.g. position of the target control with respect to the target zone).

For example, the user movement data may relate to tilt data monitored and received in response to the dynamic environment during a session. In the example shown in FIG. 2B, the user movement data is represented by the dash line. In some embodiments, the performance variable(s) based on user movement data may include control fluidity variable(s), error response variable(s), among others, or a combination thereof. The control fluidity variables may relate to a measure of motor control, for example, it may be measure of smoothness of user movement. In some embodiments, the one or more control fluidity variables may include but are not limited to user jerkiness, dominant frequencies, movement indices, among others, or a combination thereof. User movement jerkiness may be a measurement of amount of variation in the head movements during a session or during a response to error (e.g. after an overshoot). In some embodiments, user movement jerkiness may be determined based on the magnitude of small head movements during a session. In some embodiments, the dominant frequency may relate to one or more frequencies of movement, for example, a high frequency may represent a period of high movement and a low frequency may represent a low movement.

In some embodiments, the user error response variables may relate to the user movement during a period in the error zone. For example, the user error response variables may relate to overshoot tilt response. The one or more variables may include but are not limited to time to first corrective head tilt, tilt error (or non-corrective response), response variability, response jerkiness, index measures of user control, among others, or a combination thereof. The time to first corrective head tilt may be the time between an error response (overshoot) to time when corrective user input data is determined. For example, the time may correspond to the time for when the user to tilt in a corrective direction after an overshoot. For example, if the user movement data causes the ball in the environment shown in FIG. 1 to overshoot the target zone to the right, the time to first head movement to the left is determined.

In some embodiments, the response variability may relate to the variability of the error response variability. By way of example, high response variability may represent inconsistent response to overshoots (e.g., user error). In some embodiments, the response jerkiness to the jerkiness for the time period following an overshoot (i.e., during the tilt response).

In some embodiments, the index measures of user control may include but is not limited to length of the head tilt path length (e.g., total length of user movement), user control velocity/acceleration (e.g., head tilt acceleration), entropy analysis, during a session and/or during one or more error time periods (e.g., overshoot).

In some embodiments, the target control parameters may relate to the target position with respect to the user input and the dynamic virtual environment parameters. For example, the one or more target control parameters may include but not is not limited to error variables, target zone index, target control index measures, among others, or a combination thereof. The error variables may relate to one or more overshoot variables. The one or more error variables may include but is not limited to number of overshoots (e.g., the ball enters the target zone and exits into an error zone); max distance from the balance zone during overshoot (e.g., the amplitude of ball movement away from the balance zone); path length of overshoot (e.g., the length of line that represents the target (e.g., ball) during an overshoot); duration/time for overshoot (e.g., a time that a target spends after overshooting before re-entering the target zone); overshoot "jitter" movements (e.g., movements of the ball toward and away from the target zone after an overshoot); variability of any of the error variables; among others; or a combination thereof. In some embodiments, the time in target zone may include the total time that the target spends in the target zone during a session. In some embodiments, the time in target zone may represent as a ratio of total time in target zone over session(s) time.

In some embodiments, the target control index measures correlate measures of target control movement. In some embodiments, the target control index measures may include but are not limited to target control path length (e.g., total movement of target control during a session (e.g., a solid line in FIGS. 2A and 2B); target control velocity/acceleration (the velocity and acceleration of the ball during the session); and entropy analysis (e.g., entropy is a measure of target control movement during the session).

In some embodiments, the performance assessment information may be specific to the one or more testing conditions associated with the session. In some embodiments, the sensory motor performance information may be a quantitative and/or qualitative assessment of the user's sensory motor. In some embodiments, the systems and methods may determine a sensory motor score from the performance assessment information. The sensory motor score may be a score for all sessions, a portion of the session, an individual session, or a combination thereof. For example, the score may be for all of the one or more testing conditions and/or difficulty level, a score for each of the testing conditions and/or difficulty level, and/or a combination thereof. In some embodiments, the sensory motor performance score may be a percent of the individual baseline function (e.g., 90% of a baseline) or an integer score based on normative values with the highest score representing normal sensory integration (e.g., 89 out of a possible 100).

FIGS. 4-7 show methods of determining sensory motor performance information from user movement data and system state data generated with respect to dynamic environment attributes, parameters and/or conditions according to embodiments. Unless stated otherwise as apparent from the following discussion, it will be appreciated that terms such as "comparing," "modifying," "generating," "determining," "calibrating," "displaying," "obtaining," "processing," "computing," "selecting," "receiving," "detecting," "estimating," "calculating," "quantifying," "outputting,"

"acquiring," "analyzing," "retrieving," "inputting," "moving," "assessing," "performing," or the like may refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices. The system for carrying out the embodiments of the methods disclosed herein is not limited to the systems shown in FIGS. 9 and 10. Other systems may also be used.

The methods of the disclosure are not limited to the steps described herein. The steps may be individually modified or omitted, as well as additional steps may be added. It will be also understood that at least some of the steps may be performed in parallel.

Figure 4:
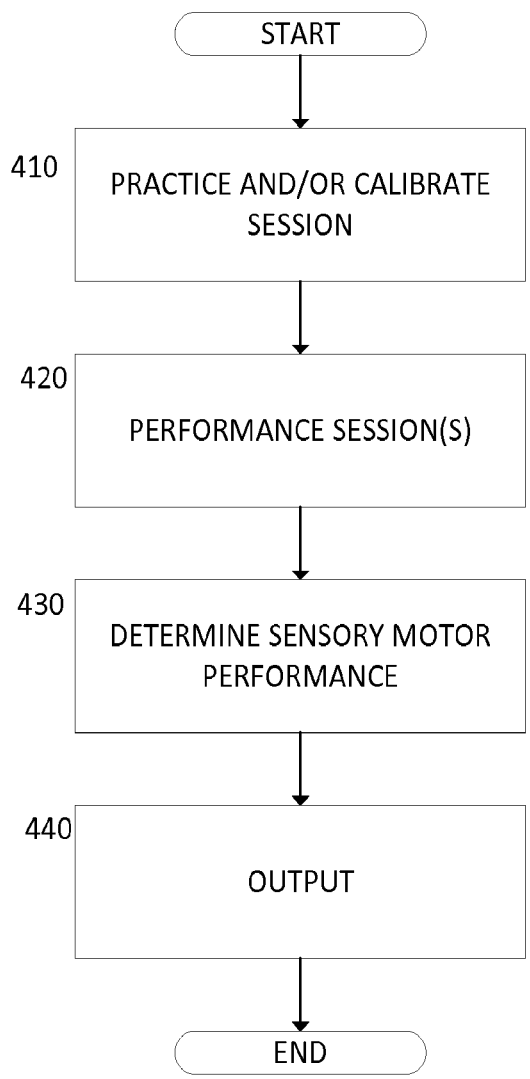
FIG. 4 shows a method of determining sensory motor performance according to embodiments.

FIG. 4 illustrates a method 400 for determining sensory motor performance information from a generated dynamic virtual environment according to one or more testing conditions. The method 400 may start, for example, by the user initiating a recreational game and/or a user initiating an sensory motor performance evaluation (e.g., after a concussion). The method 400 may include a user initiating a performance session. As shown in FIG. 4, the method 400 may include a step 410 of providing a practice session and/or a calibration session. In the practice and/or a calibration session, a dynamic virtual environment may be generated according to one or more of the testing conditions and presented to the user interface. In some embodiments, the practice session may be a baseline session. For example, during the practice and/or calibration session, the systems and methods may be provided to calibrate the system. For example, the session may be used to collect performance information to determine tilt sensitivity. During the calibration session, the system can calibrate the IMU with respect to the dynamic virtual environment based on the user movement. The systems and methods according to embodiments may adjust the dynamic virtual environment and/or the performance information based on the calibrations. The calibrations may include tilt sensitivity. In some embodiments, the systems and methods may generate a session to be used as a baseline test to determine the tilt sensitivity. Based on the determined tilt sensitivity, the system can modify the control object response to a user input (e.g., head tilt or hand tilt). For example, the system can either quicken and/or slow down the control object response, the target response, and/or a combination thereof. The performance information determined for this baseline session may be processed to determine the optimal tilt sensitivity for a user to maximize difficulty while maintaining average performance (i.e., the game is neither too easy nor too hard). For example, increasing the tilt sensitivity can cause an increase in the control object response to user movement (e.g., a head tilt). In this way, the optimal tilt sensitivity can be user specific. In some embodiments, tilt sensitivity his can also and/or alternatively be used, for example, as a baseline for future assessments. In this way, the individual characteristics of a user can be taken into account when analyzing the performance information to determine sensory motor performance. It will be understood that step 410 may be omitted.

Next, the method 400 may include a step 420 of generating one or more performance sessions to be presented to the user for determination of performance information. The performance sessions may include providing a dynamic virtual environment for each of the one or more testing conditions and at one or more difficulty levels. For example, the system may provide a session with different attributes (e.g., different target objects), status of the attributes (e.g., fixed vs. dynamic), difficulty levels, or a combination thereof.

The method 400 may include a step 430 determining sensory motor performance from the performance information determined for the session(s). In some embodiments, the method 400 may include a step 440 of outputting the sensor performance information. For example, the outputting may include but is not limited to displaying, storing, printing, transmitting, among others, or a combination thereof. In some embodiments, in response to the sensory motor performance information, the system may modify the attributes and parameters of the dynamic virtual environment and may update the dynamic virtual environment displayed to the user during the current session and/or to be displayed for the next session.

Figure 5:
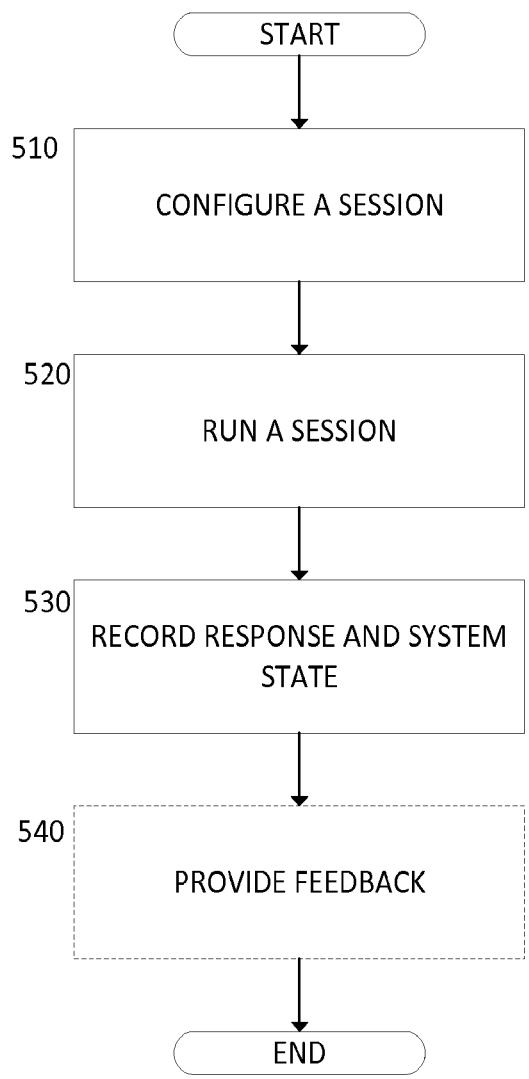
FIG. 5 shows a method of conducting sessions according to embodiments.

FIG. 5 shows a method 500 of generating a session (e.g., calibration session, practice session, and/or examination session) to collect and/or determine performance information. During the session, the user may be presented with a dynamic virtual environment on a user interface for a period of time to collect user response to the dynamic virtual environment. In some embodiments, the method 500 may include a step 510 of configuring a session for presentation to the user interface. In some embodiments, the dynamic virtual environment for the session and/or sessions may be selected from a stored collection of sessions. For example, a collection of specific sessions (e.g., sessions differing in different difficulty and/or testing conditions) may be stored and presented in succession to the user. In other embodiments, the sessions generated may be based on feedback.

In some embodiments, the method 500 may include a step 520 of running the session, for example, by presenting the dynamic virtual environment based on the one or more selected testing conditions. During the session, the method 500 may include a step 530 of recording user response and system state. For example, during the step 530, the system may detect user response to a system state and record the user input (user movement response) and system state in an associated manner, for example, with respect to an increment of time (within the session) for later processing.

In some embodiments, the method 500 may optionally include a step 540 of providing feedback. The feedback may include performance assessment information and/or sensory motor performance information associated with a period of time for one or more sessions(s). In some embodiments, the feedback may include the system modifying the dynamic virtual environment based on the current sensory motor performance information for a user (e.g., for a time period during a practice session and/or performance session). By way of example, the recorded information from step 530 may be compared to a baseline and instructions for better completing the session may be provided to the user to improve accuracy.

Figure 6:
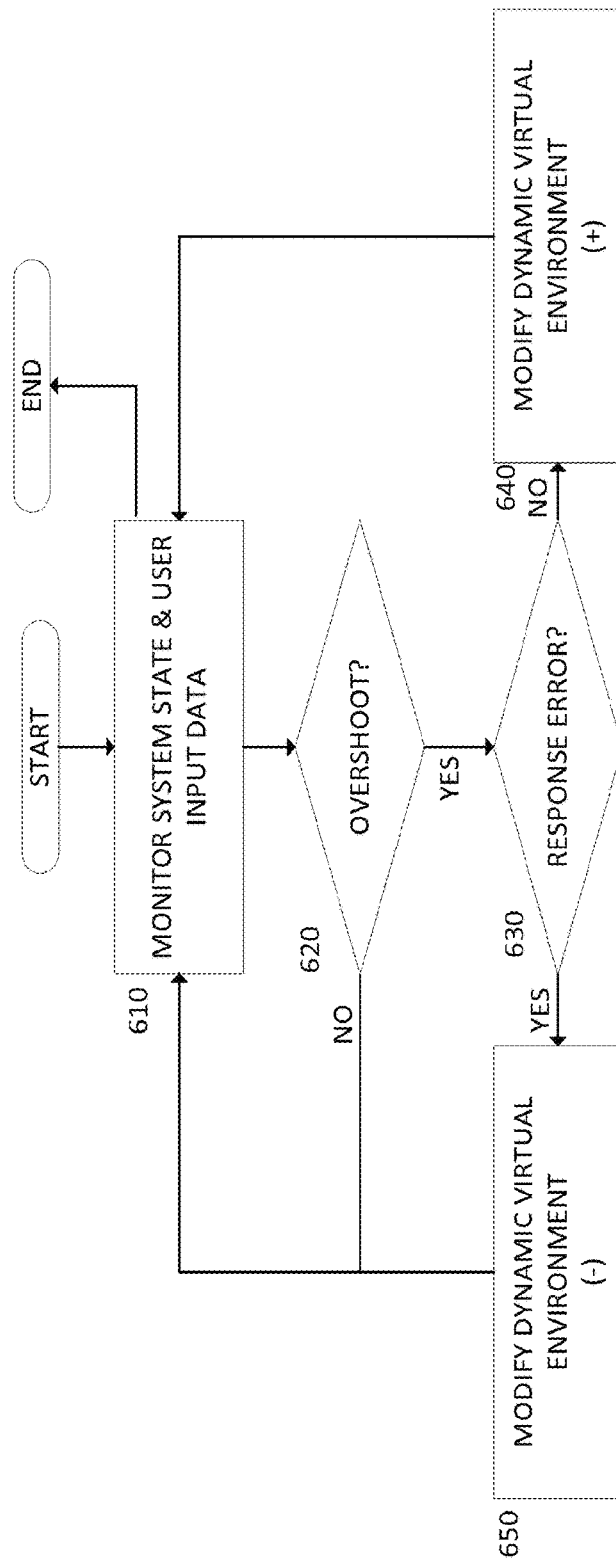
FIG. 6 shows a method of modifying the dynamic virtual environment based on performance according to embodiments.

FIG. 6 shows a method 600 of dynamically modifying the dynamic virtual environment during a session and/or for the next session based on performance assessment information. As shown in FIG. 6, the method 600 may start when a session is initiated and may end when a session is completed and/or user ends the session (e.g., by turning off the game). During the session, the method 600 may include a step 610 of continuously monitoring the system state and user input data. During the monitoring, the method 600 may include a step 620 of determining whether an overshoot (or error response) has occurred. For example, the system may determine whether the target position corresponds to the regions 224 outside the target zone 222, for example, as shown in FIGS. 2A and 2B.

If the method 600 determines that no overshoot has occurred (NO) at step 620, then the system may continue to monitor the system state and user input data (step 610) (with no modifications to the dynamic virtual environment).

If the method determines that there is an overshoot (YES) at step 620, then the method 600 may include a step 630 of determining whether there is a response error. For example, the step 630 may include determining whether if the user's movement results in one of the overshoot tilt response variables. In some embodiments, the system 600 may process the user response data during the one or more time periods associated with the overshoot to determine whether the user's movement resulted in, for example, a tilt error.

If the method 600 determines that there is no response error (NO at step 630), then the method 600 may include a step 640 of modifying the dynamic virtual environment. In some embodiments, the system may modify the dynamic virtual environment parameter(s) and cause the updated dynamic virtual environment to be displayed to the user. For example, the dynamic virtual environment may be modified to be harder, for example, by increasing the tilt sensitivity and/or target response to gravity (for example, by increasing the gravity constant). On the other hand, if the method 600 determines that there is a response error (YES at step 630), then the method 600 may include a step 650 of modifying the dynamic virtual environment, for example, to make it easier. In some embodiments, the system may modify the dynamic virtual environment parameter(s) and cause the updated dynamic virtual environment to be displayed to the user. For example, the dynamic virtual environment may be modified to be easier, for example, by decreasing the tilt sensitivity and/or target response to gravity (for example, by increasing the gravity constant).

In some embodiments, the steps 440 and 450 may also modify the difficulty level of dynamic virtual environment. In some embodiments, the modifications in steps 640 and 650 may be based on the number and/or magnitude of the response error(s). In some embodiments, the system may modify the existing dynamic virtual environment (i.e., the dynamic viral environment presented in a session) and/or may modify the dynamic virtual environment to be presented in the next session based on the one or more response errors.

Figure 8A:
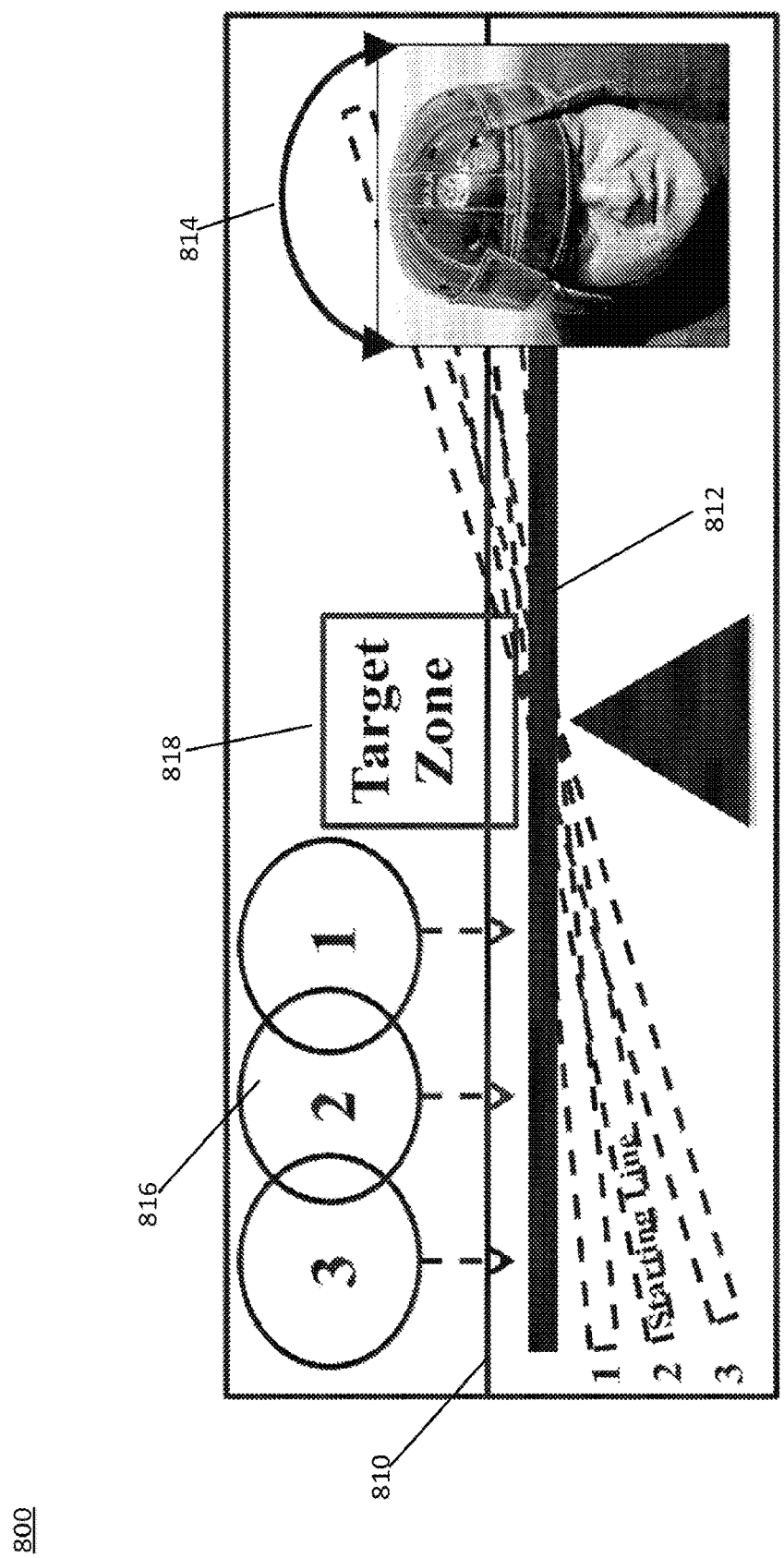
FIGS. 8A-D show examples of dynamic virtual environments having different parameters according to embodiments.

FIGS. 8A-D show examples of different dynamic virtual environments according to different testing conditions. FIG. 8A shows an example 810 of a dynamic virtual environment, which is similar to the dynamic virtual environment shown in FIG. 1, for dynamic balance ("easy" level of difficulty). For a dynamic balance testing condition for this example, the visual surround 810 (e.g., the horizon is fixed to the external horizontal environment) and the tilt system response (e.g., balance beam response to detected tilt inputs) may be fixed (e.g. the response may be predetermined). In this example, the sensory input and optical flow (e.g., vision) can be stable. The movement of the balance beam (control object) 812 can be controlled with tilt user inputs 814. The ball (target) 816 can be configured to be released onto the balance beam 812 and roll based on a physics response to gravity. In this testing condition, users can be instructed to control the ball 816, using tilt, to move the balance beam 812 to cause the rolling ball into the central "target zone" 818. In this testing condition, different difficulty levels can correspond to starting balance beam angle and variable ball response to gravity. Additionally, an attention control can be integrated into the Dynamic Balance condition and used to assess the performance, allowing for discrimination between poor performance resulting from poor motivation or inattention versus balance impairment.

Figure 8B:
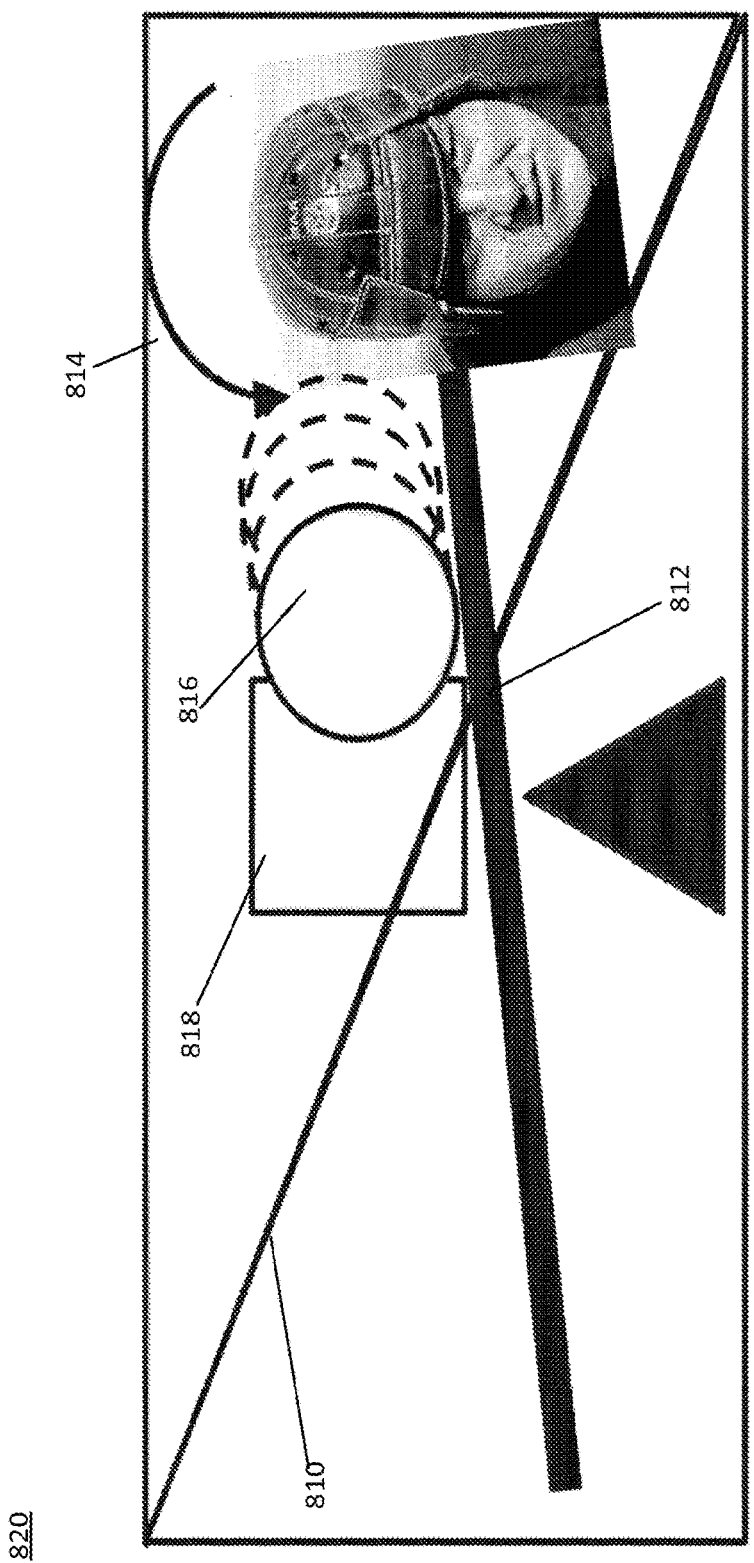
Figure 8C:
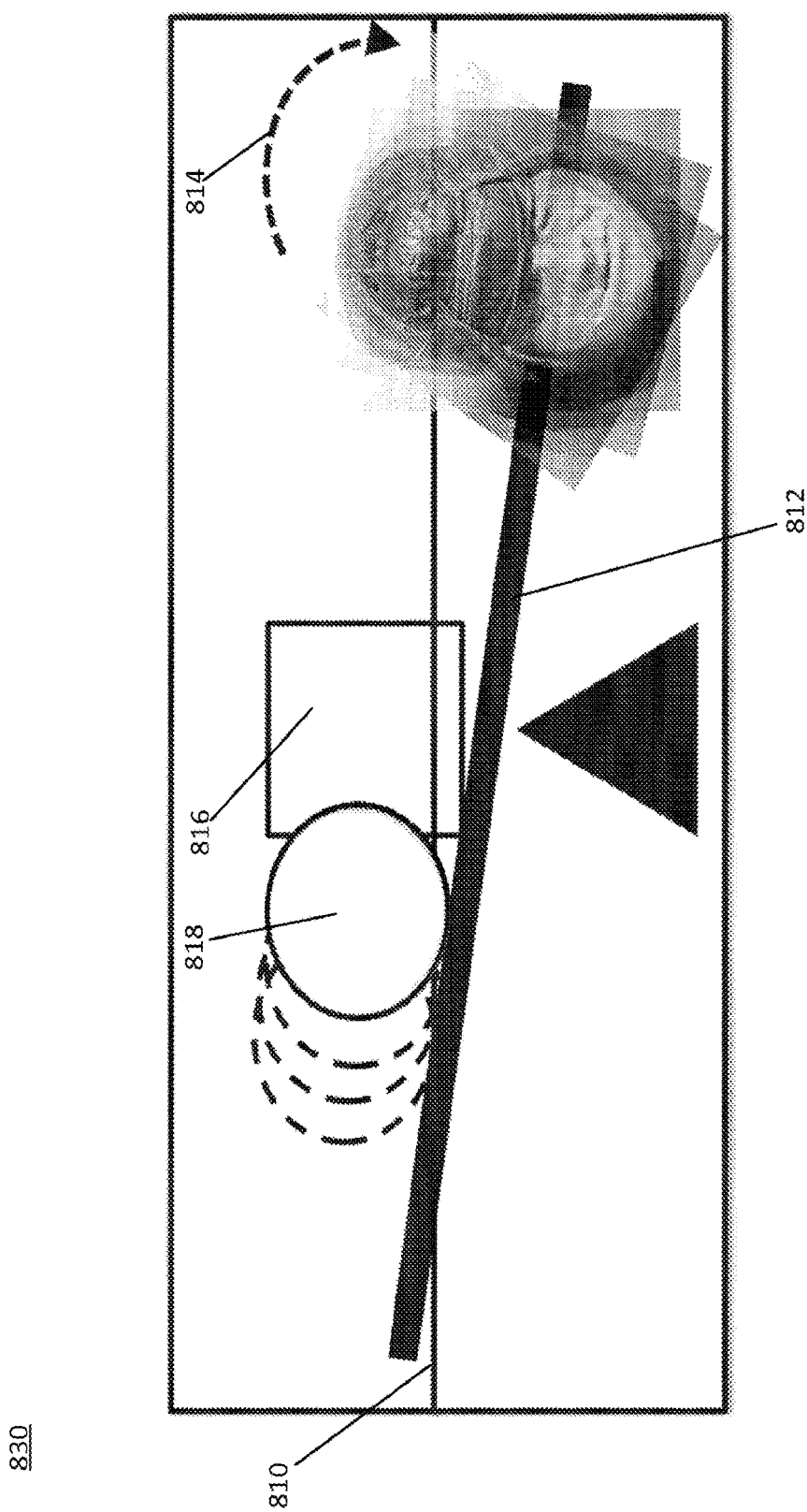

FIG. 8B shows an example 820 of a dynamic virtual environment, which has the same attributes as the dynamic virtual environment 800 shown in FIG. 8A, for optic mismatch ("medium" level of difficulty). For an optic mismatch testing condition, the visual surround 812 may be dynamic (e.g., oscillate rhythmically) rather than a fixed visual surround (shown in FIG. 8A); and the tilt system response (e.g., balance beam response to tilt inputs) may be fixed like the dynamic balance testing condition. Performance on this task can require users to avoid reliance on visual environmental cues and subjective visual horizontal vestibular inputs (e.g., from the visual surround), and overcome sway responses demonstrated to occur with rocking optic flow perturbations FIG. 8C shows an example 830, which has the same attributes as the dynamic virtual environment 800 shown in FIG. 8A, for tilt response mismatch ("hard" level of difficulty). For tilt response mismatch, the visual surround 810 may be fixed like the dynamic balance testing condition and the tilt system response (e.g., balance beam response to tilt inputs) may be dynamic. The balance beam response to tilt may be altered with tilt resulting in hyper-sensitive balance beam responses compared to the fixed beam responses like the dynamic balance testing condition. Performance on this task can require users to rapidly adapt to unanticipated balance beam responses by reprogramming tilt control with new somatosensory (proprioceptive) inputs (e.g. head/neck somatosensory inputs).

Figure 8D:
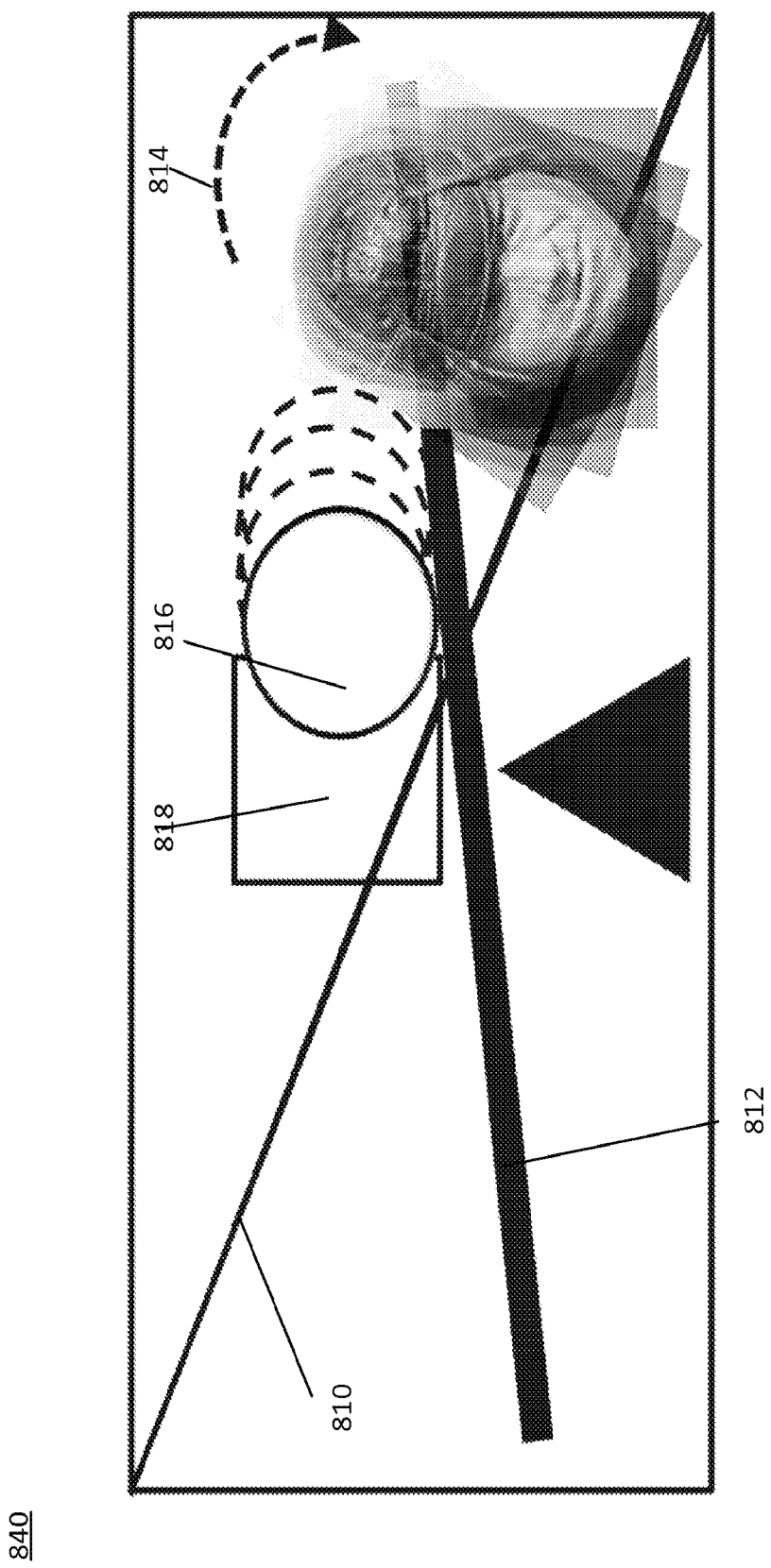

FIG. 8D shows an example 840, which has the same attributes as the dynamic virtual environment 800 shown in FIG. 8A, for optic/tilt response mismatch (also referred to as "optic flow"). For optic/tilt response mismatch, the visual surround 810 may be dynamic (e.g., oscillate rhythmically) rather than a fixed visual surround like the dynamic balance testing condition; and the tilt system response (e.g., balance beam response to tilt inputs) may be dynamic like the tilt response mismatch testing condition. Performance under this testing condition can require users to avoid reliance on visual environmental cues (e.g., the subjective visual horizontal of the visual surround), overcome visual balance responses, and rapidly adapt to unanticipated balance beam responses.

After the environment is modified, generated, and displayed to the user, the method 600 may continue to monitor the system state and user input data in view of the updated dynamic virtual environment parameters and/or conditions (step 610). The method 600 may continue to monitor for overshoots (e.g., repeat the steps) until the session is completed and/or user ends the session (e.g., by turning off the game).

Figure 7:
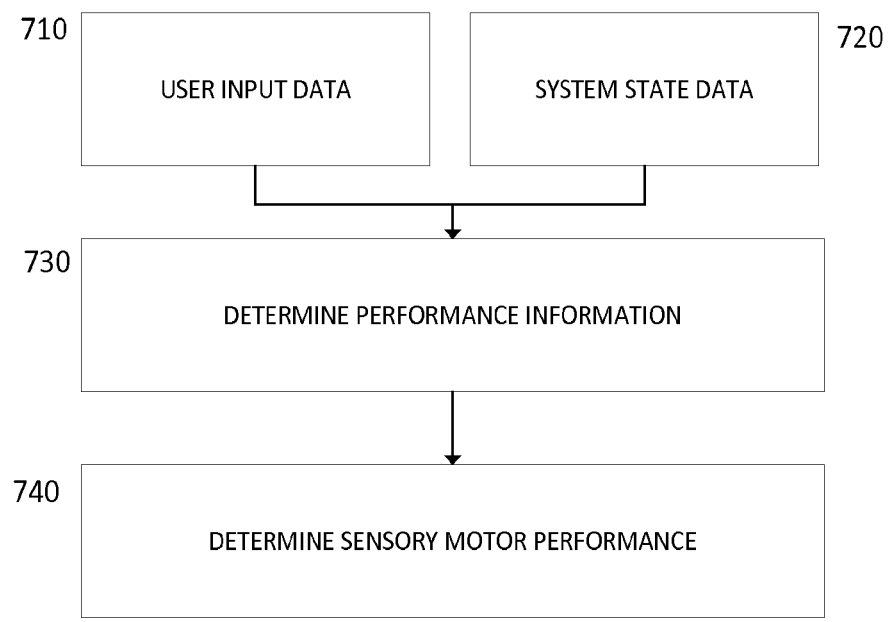
FIG. 7 shows an example of processing recorded data to determine sensory motor performance.

FIG. 7 shows a method for determining sensory motor performance information from the performance information collected during the monitoring step (620). As shown in FIG. 7, the method 700 may include a step 710 of retrieving and/or determining the user input data 710 and the system state data 720 for one or more time periods during one or more sessions. For example, the system may detect hand movement by a handheld unit and/or head movement by a head-mounted device. The method 700 may include a step 730 of determining performance assessment information based on the user input (e.g., handheld unit and/or head-mounted device) and the system state (e.g., the state of the attributes in the dynamic virtual environment). In some embodiments, the method 700 may include a step 740 for determining sensory motor performance information based on the one or more variables of the performance assessment information. The system, for example, can determine a qualitative and/or quantitative assessment of a sensory motor performance. The system may use the sensory motor performance and/or performance variables to provide feedback to the user about the performance, for example, during a recreational game (e.g., step 540) and/or use the sensory motor performance and/or performance variables to update the dynamic virtual environment for the current and/or next session (e.g., FIG. 6). The system can provide the information in real-time.

In some embodiments, the systems may threshold the sensory motor performance and/or compare the sensory motor performance to a baseline (the user baseline and/or a control baseline) to determine whether the user has a sensor motor performance problem. For example, the systems may determine a sensory motor performance score based on one or more of the performance variables, which may be indicative of a balance problem. In some embodiments, the system may include a threshold for the balance score. For example, the threshold may be a value and/or a range of values added to the balance score. A user having those values within the threshold may not be considered a sensory motor performance problem.

Figure 9:
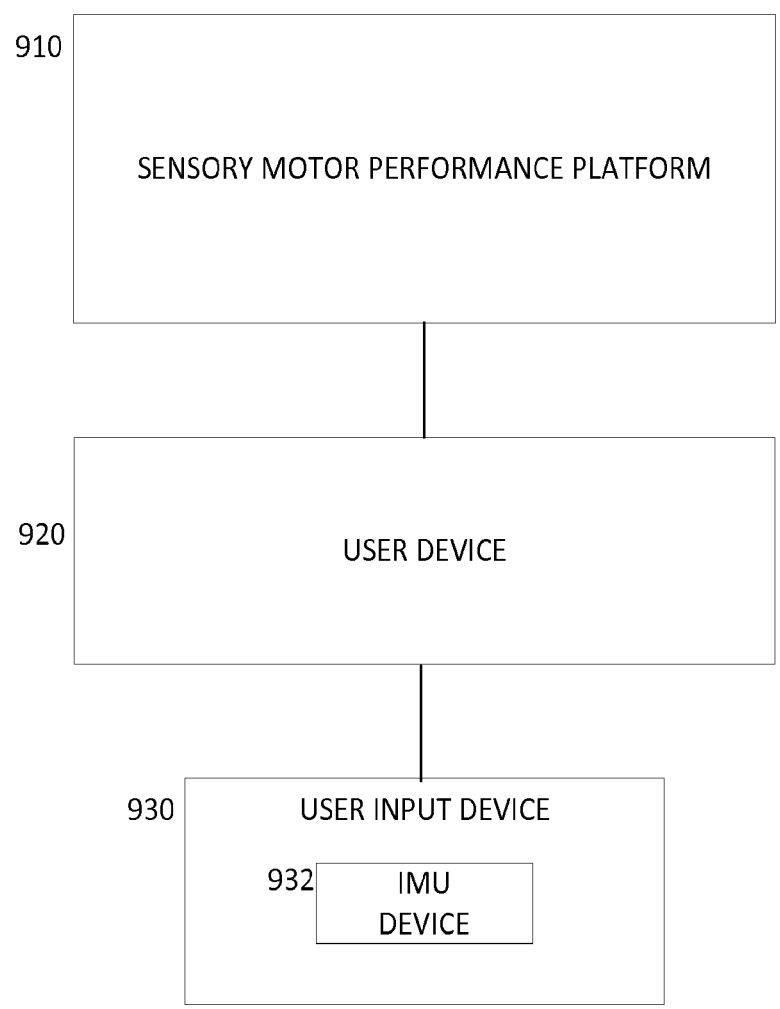
FIG. 9 shows a block diagram illustrating a system according to embodiments.

FIG. 9 shows a system 900 capable of providing a dynamic virtual environment configured to determine sensory motor performance. The system 900 may include any number of modules that communicate with other through electrical or data connections (not shown). In some embodiments, the modules may be connected via a wired network, wireless network, or a combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radio frequency network, or another similarly functioning wireless network. In some embodiments, any of the modules and/or systems of the system 900 may be at least in part be based on cloud computing architecture. In some embodiments, the modules and/or systems may be applied to a self-hosted private cloud based architecture, a dedicated public cloud, a partner-hosted private cloud, as well as any cloud based computing architecture.

Although the modules of the system are shown as being directly connected, the modules may be indirectly connected to one or more of the other modules of the system. In some embodiments, a module may be only directly connected to one or more of the other modules of the system. It is also to be understood that the system may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

As shown in FIG. 9, the system 900 may include a user device 910. In some embodiments, the user device 910 may be a portable immersive system. The portable immersive system may include a wearable user interface (e.g., glasses or goggles) having an optical head-mounted display, headphones, and a portable computing device. In some embodiments, the user device 910 may include and/or correspond to a different portable computing device (e.g., a mobile device, smart phone, tablet device, laptop, other portable computing devices etc.), portable immersive system (e.g., such as includes a wearable glasses or goggles having an optical head-mounted display, headphones, portable computing device, etc.), etc., among others, or a combination thereof. The user device 910 may include and/or communicate with a user input device 930 configured for non-postural movement. The user input device 930 may include one or more IMU devices 932 to detect user inputs (e.g., user movement) relative to the dynamic environment. In some embodiments, the user input device 930 may be integrated into the user device 910. For example, a head mounted display may be capable of detecting head movement and a hand-held tablet and/or smart phone may be capable of detecting hand movement. The one or more IMU 932 may include a sensor configured to detect movement, such an accelerometer sensitive to user head tilt, for example, that is incorporated into the wearable user interface and/or via a separate handheld unit accelerometer sensitive to tilting of the handheld unit by user hand motion, as well as other sensors (e.g., gryometer, inclinometer, and the like). The one or more IMU 932 may include but is not limited to an accelerometer, gyroscope, magnetometer, among others, or a combination thereof. In some embodiments, the user input device 930 may be separate from the user device 910 configured to display and generate the dynamic virtual environment.

In some embodiments, the system 900 may include a platform 920 configured to generate the dynamic virtual environment and determine sensory motor performance according to embodiments. In some embodiments, the user device 910 may include an application suite that can perform all or a portion of the functions of the platform 920. In some embodiments, the application suite may include any type of application that can be executed on the user device 910. In some embodiments, an application performing all or a portion of the functions of the platform 920 may be downloadable. In one embodiment, the platform 920 may interface with one or more of the applications on the user device 910 to perform one or more functions described herein. In some embodiments, the platform 920 may be capable of running in the background of another application to determine sensory motor performance.

Figure 10:
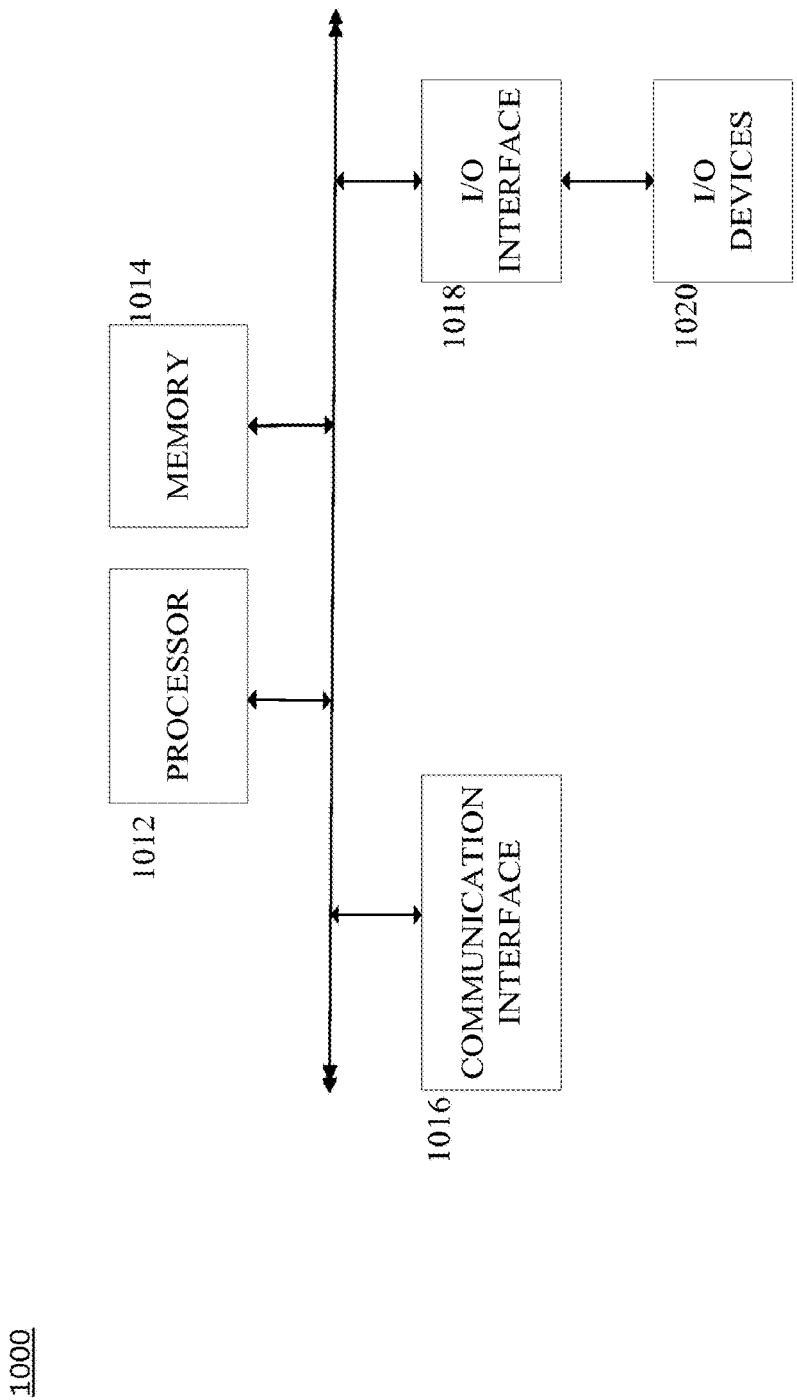
FIG. 10 shows a block diagram illustrating an example of a computing system.

One or more of the modules and/or systems of system 900 may be and/or include a computer system and/or device. FIG. 10 is a block diagram showing a computer system 1000. The modules of the computer system 1000 may be included in at least some of the systems and/or modules, as well as other devices of system 900.

The systems may include any number of modules that communicate with other through electrical or data connections (not shown). In some embodiments, the modules may be connected via a wired network, wireless network, or combination thereof. In some embodiments, the networks may be encrypted. In some embodiments, the wired network may be, but is not limited to, a local area network, such as Ethernet, or wide area network. In some embodiments, the wireless network may be, but is not limited to, any one of a wireless wide area network, a wireless local area network, a Bluetooth network, a radiofrequency network, or another similarly functioning wireless network.

It is also to be understood that the systems may omit any of the modules illustrated and/or may include additional modules not shown. It is also be understood that more than one module may be part of the system although one of each module is illustrated in the system. It is further to be understood that each of the plurality of modules may be different or may be the same. It is also to be understood that the modules may omit any of the components illustrated and/or may include additional component(s) not shown.

In some embodiments, the modules provided within the systems may be time synchronized. In further embodiments, the systems may be time synchronized with other systems, such as those systems that may be on the medical facility network.

The system 1000 may be a computing system, such as a workstation, computer, or the like. The system 1000 may include one or more processors 1012. The processor(s) 1012 (also referred to as central processing units, or CPUs) may be any known central processing unit, a processor, or a microprocessor. The CPU 1012 may be coupled directly or indirectly to one or more computer-readable storage media (e.g., memory) 1014. The memory 1014 may include random access memory (RAM), read only memory (ROM), disk drive, tape drive, etc., or a combinations thereof. The memory 1014 may be configured to store programs and data, including data structures. In some embodiments, the memory 1014 may also include a frame buffer for storing data arrays.

In some embodiments, another computer system may assume the data analysis or other functions of the CPU 1012. In response to commands received from an input device, the programs or data stored in the memory 1014 may be archived in long term storage or may be further processed by the processor and presented on a display.

In some embodiments, the system 1010 may include a communication interface 1016 configured to conduct receiving and transmitting of data between other modules on the system and/or network. The communication interface 1016 may be a wired and/or wireless interface, a switched circuit wireless interface, a network of data processing devices, such as LAN, WAN, the internet, or combination thereof. The communication interface may be configured to execute various communication protocols, such as Bluetooth, wireless, and Ethernet, in order to establish and maintain communication with at least another module on the network.

In some embodiments, the system 1010 may include an input/output interface 1018 configured for receiving information from one or more input devices 1020 (e.g., a keyboard, a mouse, and the like) and/or conveying information to one or more output devices 1020 (e.g., a printer, a CD writer, a DVD writer, portable flash memory, etc.). In some embodiments, the one or more input devices 1020 may configured to control, for example, the generation of the dynamic virtual environment according to one or more testing conditions and/or user input, presentation of the dynamic virtual environment in the user interface, generation and/or display of the balance performance information among other things.

In some embodiments, the disclosed methods (e.g., FIGS. 4-7) may be implemented using software applications that are stored in a memory and executed by a processor (e.g., CPU) provided on the system 1000. In some embodiments, the disclosed methods may be implanted using software applications that are stored in memories and executed by CPUs distributed across the system 1000. As such, any of the systems and/or modules of the system 1000 may be a general purpose computer system, such as system 1000, that becomes a specific purpose computer system when executing the routine of the disclosure. The systems and/or modules of the system 1000 may also include an operating system and micro instruction code. The various processes and functions described herein may either be part of the micro instruction code or part of the application program or routine (or combination thereof) that is executed via the operating system.

If written in a programming language conforming to a recognized standard, sequences of instructions designed to implement the methods may be compiled for execution on a variety of hardware platforms and for interface to a variety of operating systems. In addition, embodiments are not described with reference to any particular programming language. It will be appreciated that a variety of programming languages may be used to implement embodiments of the disclosure. An example of hardware for performing the described functions is shown in FIGS. 9 and 10.

It is to be further understood that, because some of the constituent system components and method steps depicted in the accompanying figures can be implemented in software, the actual connections between the systems components (or the process steps) may differ depending upon the manner in which the disclosure is programmed. Given the teachings of the disclosure provided herein, one of ordinary skill in the related art will be able to contemplate these and similar implementations or configurations of the disclosure.

While the disclosure has been described in detail with reference to exemplary embodiments, those skilled in the art will appreciate that various modifications and substitutions may be made thereto without departing from the spirit and scope of the disclosure as set forth in the appended claims. For example, elements and/or features of different exemplary embodiments may be combined with each other and/or substituted for each other within the scope of this disclosure and appended claims.

What is claimed is:

1. A method of determining balance performance, comprising:

receiving performance information for a user with respect to a dynamic virtual environment provided on a user interface for one or more sessions, the performance information for the one or more sessions including i) user input data with respect to a state of one or more attributes of a dynamic virtual environment for the one or more sessions and ii) the state of the one or more attributes for the one or more sessions, wherein:

the user input data relates to non-postural movement of the user detected by a user input device;

the one or more attributes includes a control object, a target, and a target zone;

an objective of the dynamic virtual environment includes the target to be moved within the target zone, within the dynamic virtual environment, a position and a movement of the control object is controlled by the user input data, a position and a movement of the target is with respect to the control object and is determined using the position and the movement of the control object, and the target zone is a region of the control object; and the state of the one or more attributes includes the position and the movement of the target and the position and the movement of the control object;

determining one or more performance variables based on the performance information, the one or more performance variables including at least one performance variable using the position and/or the movement of the target with respect to the target zone; and determining sensory motor performance information from the one or more performance variables.

2. The method according to claim 1, further comprising:
generating the dynamic virtual environment based on one or more testing conditions and/or one or more levels of difficulty for the one or more sessions;
the one or more attributes of the dynamic virtual environment being fixed and/or dynamic based on the one or more testing conditions and/or the one or more levels of difficulty; and
providing the dynamic virtual environment to the user interface.

3. The method according to claim 2, wherein the one or more attributes further includes a visual surround, the method further comprising:
detecting user input with respect to the state of the one or more attributes.

4. The method according to claim 1, wherein the sensory motor performance information is a quantitative assessment and/or a qualitative assessment of the user.

5. The method according to claim 4, wherein the sensory motor performance information includes a sensory motor performance score.

6. The method according to claim 1, wherein:
the user input device and the user interface are disposed on a wearable device; and
the user input data relates to head and/or neck movements of the user detected by the user input device with respect to the dynamic virtual environment.

7. The method according to claim 1, wherein:
the one or more attributes includes one or more regions of the control object that are outside of the target zone; and
the one or more performance variables includes a response error that is based on the position and/or movement of the target with respect to the target zone and the one or more regions.

8. The method according to claim 7, further comprising:
monitoring the user input data with respect to the state of one or more attributes of the dynamic virtual environment and the state of the one or more attributes of the dynamic virtual environment during at least one session of the one or more sessions;
determining whether the target is in the one or more regions that is outside of the target zone;
if the target is in the one or more regions that are outside of the target zone, determining whether there is one or more response errors based on the user input data when the target is in the one or more regions that is outside of the target zone; and
modifying the dynamic virtual environment for at least one session and/or another session of the one or more sessions based on the determination of the one or more response errors.

9. The method according to claim 1, wherein
the at least one performance variable is determined using the user input data associated with at least one period of the one or more sessions when the target is outside the target zone; and
the one or more performance variables includes a first corrective head tilt, a tilt error, a response variability, a response jerkiness, and one or more index measures of user control, or a combination thereof.

10. The method according to claim 1, wherein the one or more performance variables includes at least one performance variable relating to an amount of variation within the user input data with respect to (i) at least one session and/or (ii) the position and/or the movement of the target with respect to the target zone.

11. A system for determining balance performance, comprising:
at least one processor; and
a memory, wherein the processor is configured to cause:
receiving performance information for a user with respect to a dynamic virtual environment provided on a user interface for one or more sessions, the performance information for one or more sessions including i) user input data with respect to a state of one or more attributes of a dynamic virtual environment for one or more sessions and ii) the state of the one or more attributes for one or more sessions, wherein:
the user input data relates to non-postural movement of the user detected by a user input device;
the one or more attributes includes a control object, a target, and a target zone;
an objective of the dynamic virtual environment includes the target to be moved within the target zone;
within the dynamic virtual environment, a position and a movement of the control object is controlled by the user input data, a position and a movement of the target is with respect to the control object and is determined using the position and the movement of the control object, and the target zone is a region of the control object; and
the state of the one or more attributes includes the position and the movement of the target and the position and the movement of the control object;
determining one or more performance variables based on the performance information, the one or more performance variables including at least one performance variable using the position and/or the movement of the target with respect to the target zone; and
determining sensory motor performance information from the one or more performance variables.

12. The system according to claim 11, wherein the processor is further configured to cause:
generating the dynamic virtual environment based on one or more testing conditions and/or one or more levels of difficulty for the one or more sessions;
the one or more attributes of the dynamic virtual environment being fixed and/or dynamic based on the one or more testing conditions and/or the one or more levels of difficulty; and
providing the dynamic virtual environment to the user interface.

13. The system according to claim 12, wherein the one or more attributes further includes a visual surround, and the processor is further configured to cause:
detecting user input with respect to the state of the one or more attributes.

14. The system according to claim 11, wherein the sensory motor performance information is a quantitative assessment and/or a qualitative assessment of the user.

15. The system according to claim 14, wherein the sensory motor performance information includes a sensory motor performance score.

16. The system according to claim 11, wherein:
the user input device and the user interface are disposed on a wearable device; and
the user input data relates head and/or neck movements of the user detected by the user input device with respect to the dynamic virtual environment.

17. The system according to claim 11, wherein:
the one or more attributes includes one or more regions of the control object that is outside of the target zone; and
the one or more performance variables includes a response error that is based on the position and/or the movement of the target with respect to the target zone and the one or more regions.

18. The system according to claim 17, wherein the processor is further configured to cause:
monitoring (i) the user input data with respect to the state of one or more attributes of the dynamic virtual environment and (ii) the state of the one or more attributes of the dynamic virtual environment, during at least one session of the one or more sessions;
determining whether the target is in the one or more regions that is outside the target zone;
if the target is in the one or more regions that are outside of the target zone, determining whether there is one or more response errors based on the user input data when the target is in the one or more regions that is outside the target zone; and
modifying the dynamic virtual environment for the at least one session and/or another session of the one or more sessions based on the determination of the one or more response errors.

19. The system according to claim 11, wherein:
the at least one performance variable is determined using the user input data associated with at least one period of the one or more sessions when the target is outside the target zone; and
the one or more performance variables includes a first corrective head tilt, a tilt error, a response variability, a response jerkiness, one or more index measures of user control, and/or a combination thereof.

20. The system according to claim 11, wherein the one or more performance variables includes at least one performance variable relating to an amount of variation within the user input data with respect to (i) at least one session and/or (ii) the position and/or the movement of the target with respect to the target zone.

* * * * *